United States Patent
Yuan et al.

(10) Patent No.: US 9,266,204 B2
(45) Date of Patent: Feb. 23, 2016

(54) ASSEMBLY MACHINE FOR VENTING CAP OF DISPOSABLE CELL CULTURE FLASK

(75) Inventors: Jianhua Yuan, Guangzhou (CN); Yejames Yuan, Guangzhou (CN)

(73) Assignee: GUANGZHOU JIETE BIOFITER PRODUCTS CO. LTD., Guangzhou, Guangdong Province (CN)

( * ) Notice: Subject to any disclaimer, the term of this patent is extended or adjusted under 35 U.S.C. 154(b) by 271 days.

(21) Appl. No.: 13/882,164

(22) PCT Filed: Mar. 10, 2012

(86) PCT No.: PCT/CN2012/072160
§ 371 (c)(1),
(2), (4) Date: Apr. 26, 2013

(87) PCT Pub. No.: WO2013/107084
PCT Pub. Date: Jul. 25, 2013

(65) Prior Publication Data
US 2013/0306241 A1    Nov. 21, 2013

(51) Int. Cl.
*B23P 21/00* (2006.01)
*B23P 19/04* (2006.01)
*C12M 1/24* (2006.01)
*C12M 1/00* (2006.01)
*C12M 1/36* (2006.01)

(52) U.S. Cl.
CPC ............... *B23P 21/00* (2013.01); *B23P 19/04* (2013.01); *C12M 23/08* (2013.01); *C12M 23/28* (2013.01); *C12M 23/38* (2013.01); *C12M 23/50* (2013.01); *C12M 29/04* (2013.01); *C12M 41/48* (2013.01)

(58) Field of Classification Search
CPC .................................. B23P 19/04; B23P 21/00
USPC ............... 156/362, 367, 556, 569; 435/288.1
See application file for complete search history.

(56) References Cited

U.S. PATENT DOCUMENTS

| 5,036,569 A | * | 8/1991 | Linnecke | 29/33 K |
| 5,080,736 A | * | 1/1992 | Matsui | 156/64 |
| 2006/0005917 A1 | * | 1/2006 | Alvarez | 156/215 |

FOREIGN PATENT DOCUMENTS

| CN | 1631654 A | 6/2005 |
| CN | 101537999 A | 9/2009 |
| CN | 102248397 A | 11/2011 |
| JP | 2002-326129 A | 11/2002 |
| WO | 94/26461 A1 | 11/1994 |

OTHER PUBLICATIONS

International Search Report dated Aug. 30, 2012, issued in counterpart International Application No. PCT/CN2012/072160.

* cited by examiner

*Primary Examiner* — George Koch
(74) *Attorney, Agent, or Firm* — Novak Druce Connolly Bove + Quigg LLP

(57) ABSTRACT

An assembly machine for venting cap of disposable cell culture flask includes a rack, and an automatic controller and a rotating table arranged on the rack. An automatic loading mechanism, an automatic filter disc-sucking mechanism, an automatic heat-sealing mechanism, and an automatic unloading mechanism are all arranged above the rotating table. The automatic controller is electrically connected with the rotating table, the automatic loading mechanism, the automatic filter disc-sucking mechanism, the automatic heat-sealing mechanism, and the automatic unloading mechanism. By way of the automatic loading mechanism, the automatic filter disc-sucking mechanism, the automatic heat-sealing mechanism, and the automatic unloading mechanism as well as the automatic controller adapted thereto, the assembly machine can realize the automatic loading of the venting cap of disposable cell culture flask, the automatic placing of the filter disc, and the automatic heat-sealing of the venting cap of disposable cell culture flask and the filter disc, so that the automatic production of the venting cap of disposable cell culture flask can be realized.

17 Claims, 8 Drawing Sheets

ASSEMBLY MACHINE FOR VENTING CAP OF DISPOSABLE CELL CULTURE FLASK

CROSS-REFERENCE TO RELATED APPLICATIONS

This application is filed under 35 U.S.C. 371 as a U.S. national phase application of PCT/CN2012/072160, having an international filing date of 10 Mar. 2012, which claims the benefit of Chinese Patent Application No. 20120013939.2, having a filing date of 17 Jan. 2012, both of which are hereby incorporated by reference.

FIELD OF THE INVENTION

The present invention relates to an automation device, especially to an assembly machine for venting cap of disposable cell culture flask.

BACKGROUND OF THE INVENTION

The venting cap of disposable cell culture flask needs to provided with filter disc. Currently, the production of the venting cap is semi-automatic, and the production process mainly includes two steps: first, preparing a strip-shaped filter sheet and putting it on a blanking mould to punch a filter disc of a desired shape, then putting the filter disc to a predetermined position of the venting cap manually; second, arranging the venting cap with the mounted filter disc on the heat-sealing device, so that the bonding and connection of the venting cap and the filter disc can be realized through heat-sealing.

The current production of the venting cap of disposable cell culture flask has the following disadvantages: first, the production of the products is semi-automatic, and the semi-finished products need to be carried from a blanking device to a heat-sealing device, so that the turnover time of the products during production is extended, so is the production time, thereby leading to a low productivity; second, since the filter disc is manually put into the venting cap, the phenomenon that filter disc in the venting cap is in an incorrect position occurs frequently during the operation process. Therefore, there are defective products after bonding through heat-sealing, resulting in a low yield of finished products.

SUMMARY

The technical problem that the present invention aims to solve is to provide an assembly machine for venting cap of disposable cell culture flask which can realize the automatic production of the venting cap of disposable cell culture flask and improve yield of product.

The technical scheme of the present invention to solve the above-mentioned technical problem is: an assembly machine for venting cap of disposable cell culture flask, which comprises a rack, and an automatic controller and a rotating table arranged on the rack, wherein an automatic loading mechanism, an automatic filter disc-sucking mechanism, an automatic heat-sealing mechanism and an automatic unloading mechanism are all arranged above the rotating table; and the automatic controller is electrically connected with the rotating table, the automatic loading mechanism, the automatic filter disc-sucking mechanism, the automatic heat-sealing mechanism, and the automatic unloading mechanism.

As a further improvement of the technical scheme of the present invention, the present invention further comprises a lifting platform arranged above the rotating table, wherein the automatic loading mechanism, the automatic filter disc-sucking mechanism and the automatic unloading mechanism are arranged on the lifting platform orderly; and the automatic heat-sealing mechanism is arranged between the automatic filter disc-sucking mechanism and the automatic unloading mechanism.

As a further improvement of the technical scheme of the present invention, a loading guiding rail is arranged within the automatic loading mechanism, one end of the loading guiding rail is fixed on the lifting platform and the other end is hanging; a loading sliding block is arranged on the loading guiding rail; and a loading arm is arranged below the loading sliding block.

As a further improvement of the technical scheme of the present invention, a filter disc-sucking guiding rail is arranged within the automatic filter disc-sucking mechanism, one end of the filter disc-sucking guiding rail is fixed on the lifting platform and the other end is hanging; a filter disc-sucking sliding block is arranged on the filter disc-sucking guiding rail; and a filter disc-sucking end is arranged on the lower end of the filter disc-sucking sliding block.

As a further improvement of the technical scheme of the present invention, the automatic heat-sealing mechanism is mounted on the rack, and a heat-sealing end capable of moving vertically is arranged within the heat-sealing mechanism.

As a further improvement of the technical scheme of the present invention, an unloading guiding rail is arranged within the automatic unloading mechanism, one end of the unloading guiding rail is fixed on the lifting platform and the other end is hanging; and an unloading sliding block is arranged on the unloading guiding rail and an unloading arm is arranged below the unloading sliding block.

As a further improvement of the technical scheme of the present invention, a plurality of positioning fixtures are arranged on the rotating table.

As a further improvement of the technical scheme of the present invention, the present invention further comprises a filter disc punching mould which is arranged below the hanging end of the filter disc-sucking guiding rail.

As a further improvement of the technical scheme of the present invention, the present invention further comprises a feeding mechanism, wherein the feeding mechanism is provided with a vibration tray and feeding channel, one end of the feeding channel is connected with the vibration tray and the other end is arranged below the hanging end of the loading guiding rail.

The beneficial effects of the present invention are: by means of the automatic loading mechanism, the automatic filter disc-sucking mechanism, the automatic heat-sealing mechanism and the automatic unloading mechanism as well as the automatic controller adapted thereto, the present invention can realize the automatic loading of the venting cap of disposable cell culture flask, the automatic placing of the filter disc and the automatic heat-sealing of the venting cap of disposable cell culture flask and the filter disc, so that the automatic production of venting cap of disposable cell culture flask can be realized.

The present invention is applicable to automatic production of venting cap of disposable cell culture flask.

DETAILED DESCRIPTION OF THE EMBODIMENTS

Figure 1:
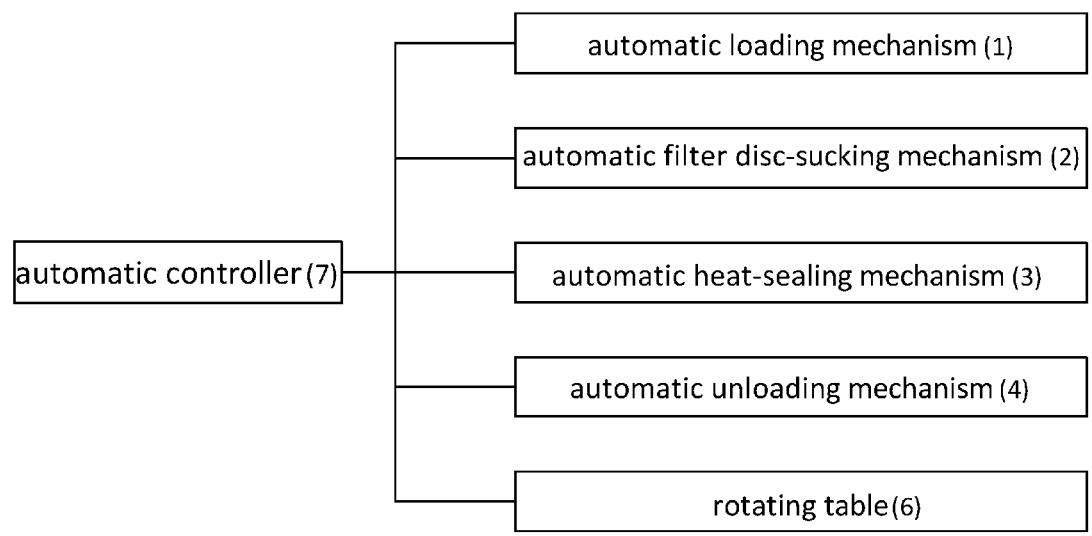
FIG. 1 is an electrical connection diagram of mechanisms of the present invention.
Figure 2:
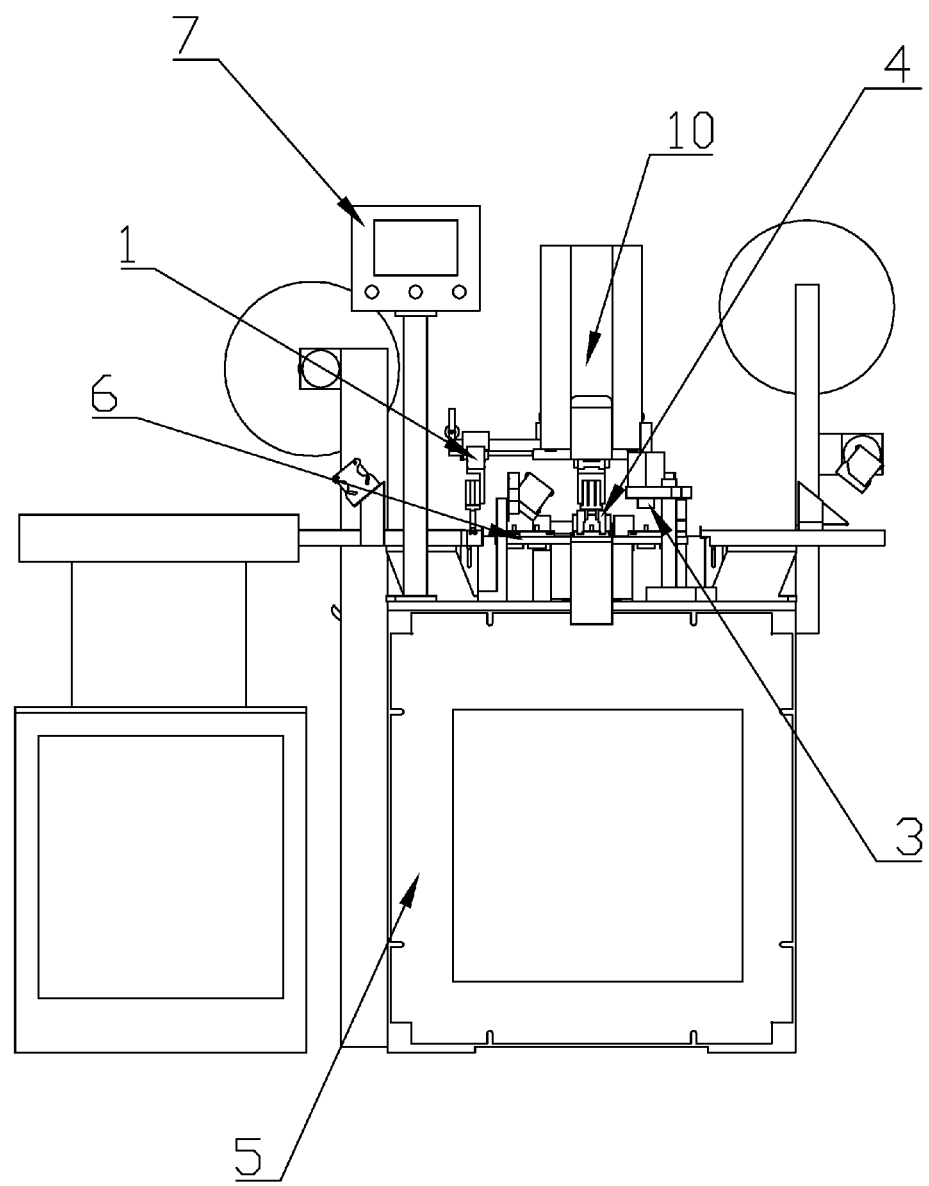
FIG. 2 is a front view of the present invention.
Figure 3:
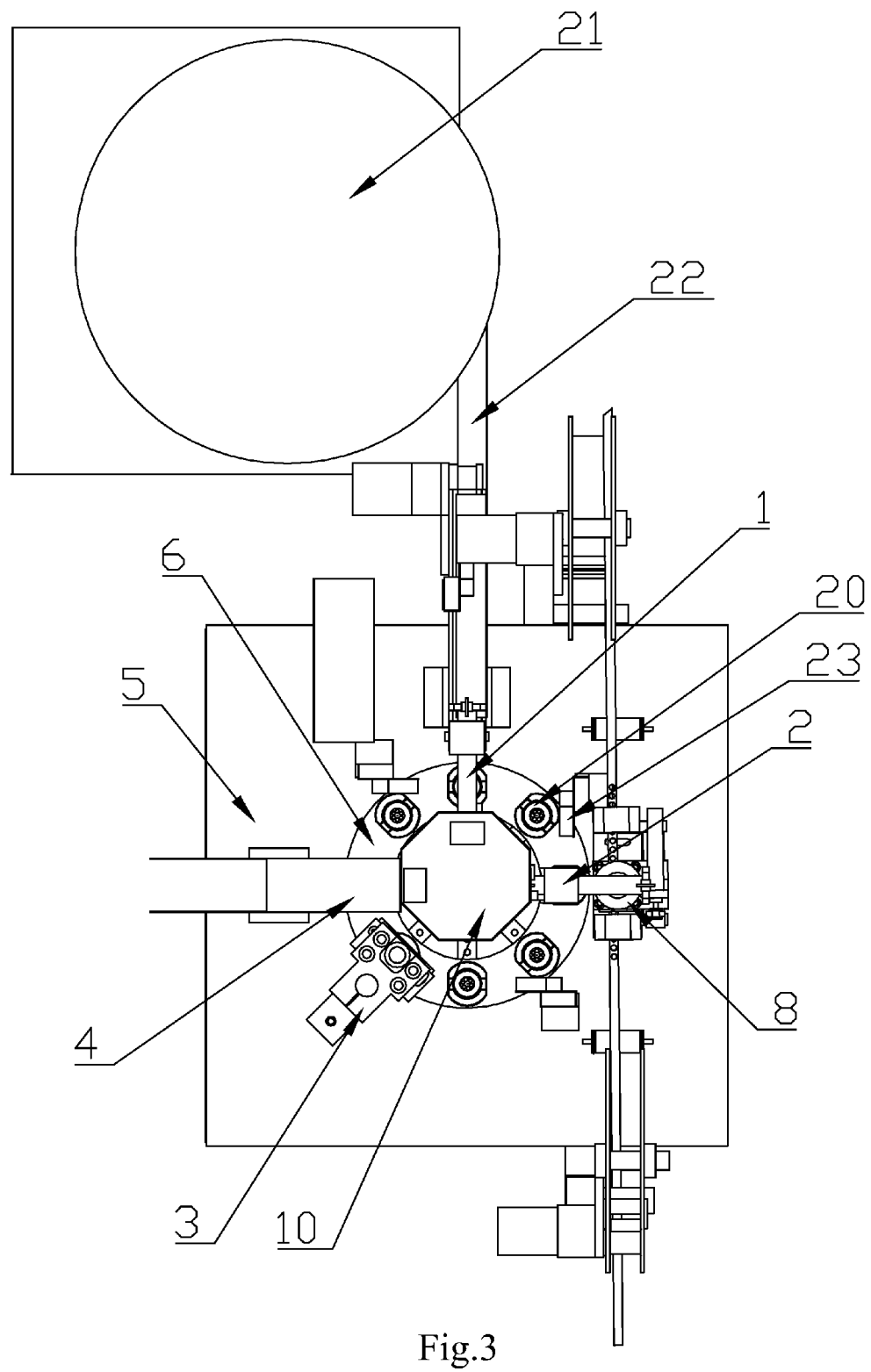
FIG. 3 is a top view of the present invention.
Figure 4:
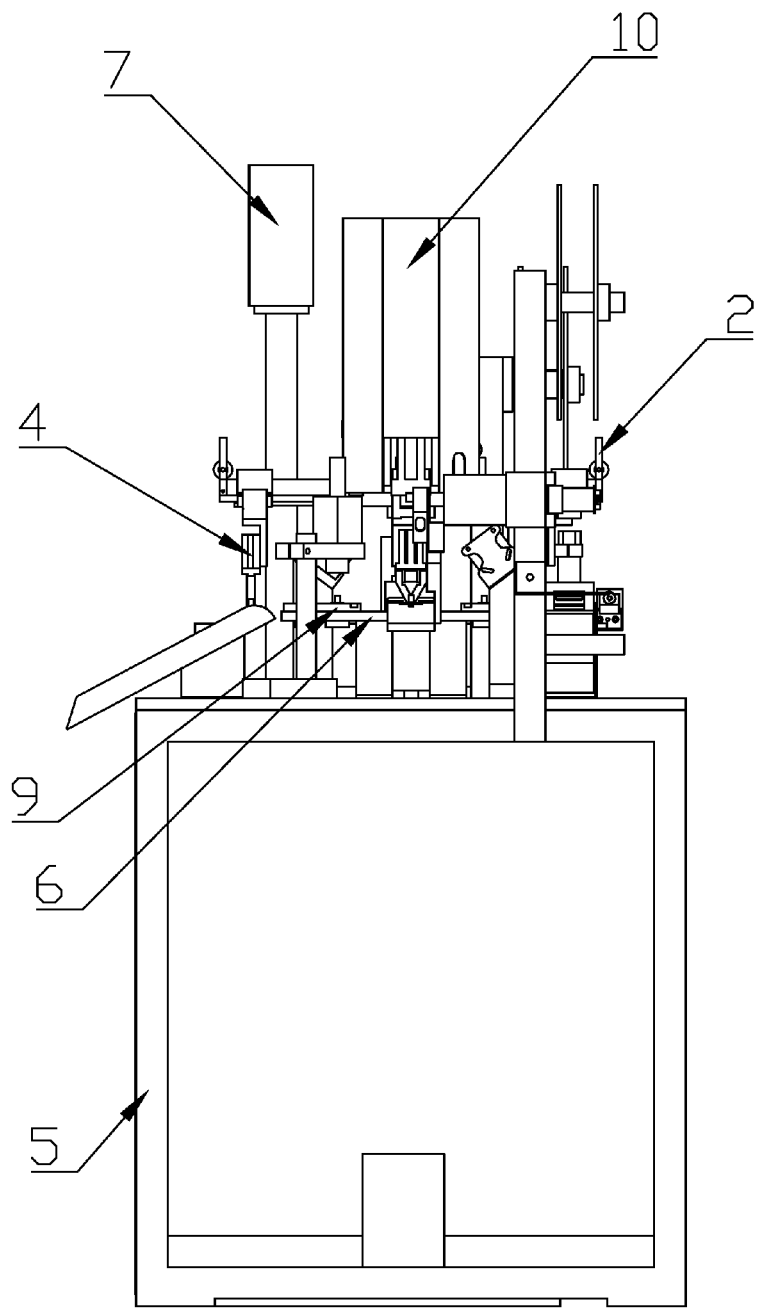
FIG. 4 is a side view of the present invention.
Figure 5:
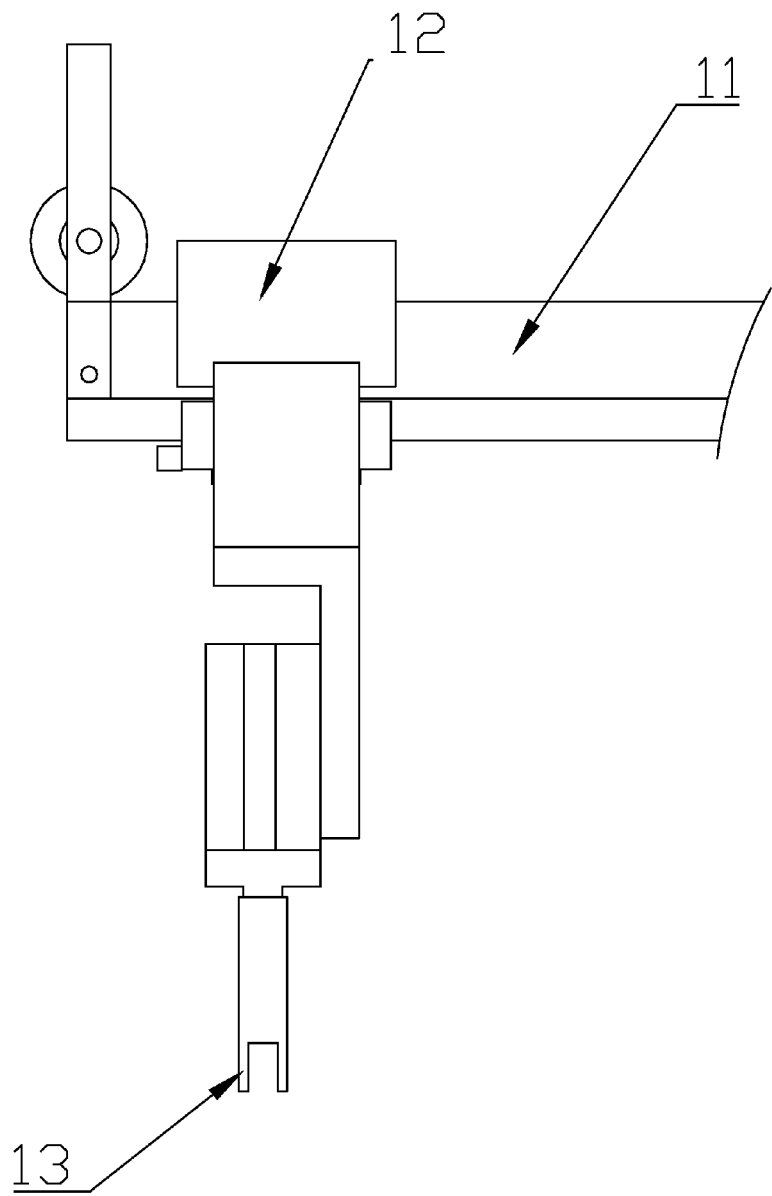
FIG. 5 is a structural schematic diagram of the automatic loading mechanism of the present invention.
Figure 6:
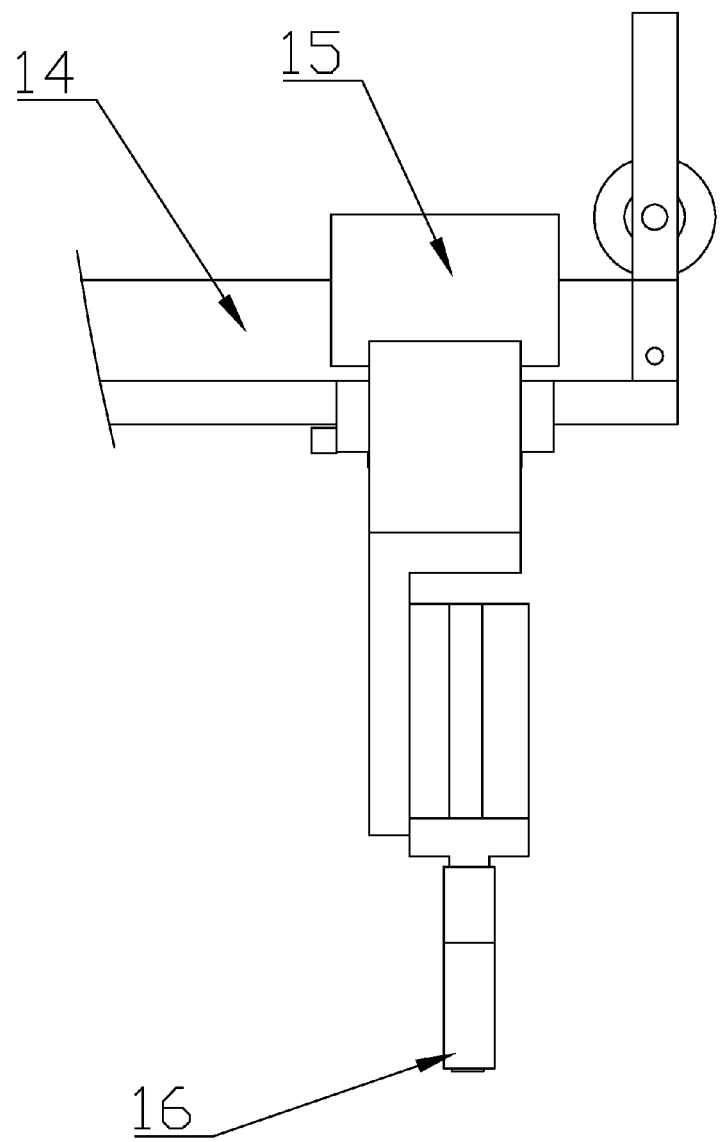
FIG. 6 is a structural schematic diagram of the automatic filter disc-sucking mechanism of the present invention.
Figure 7:
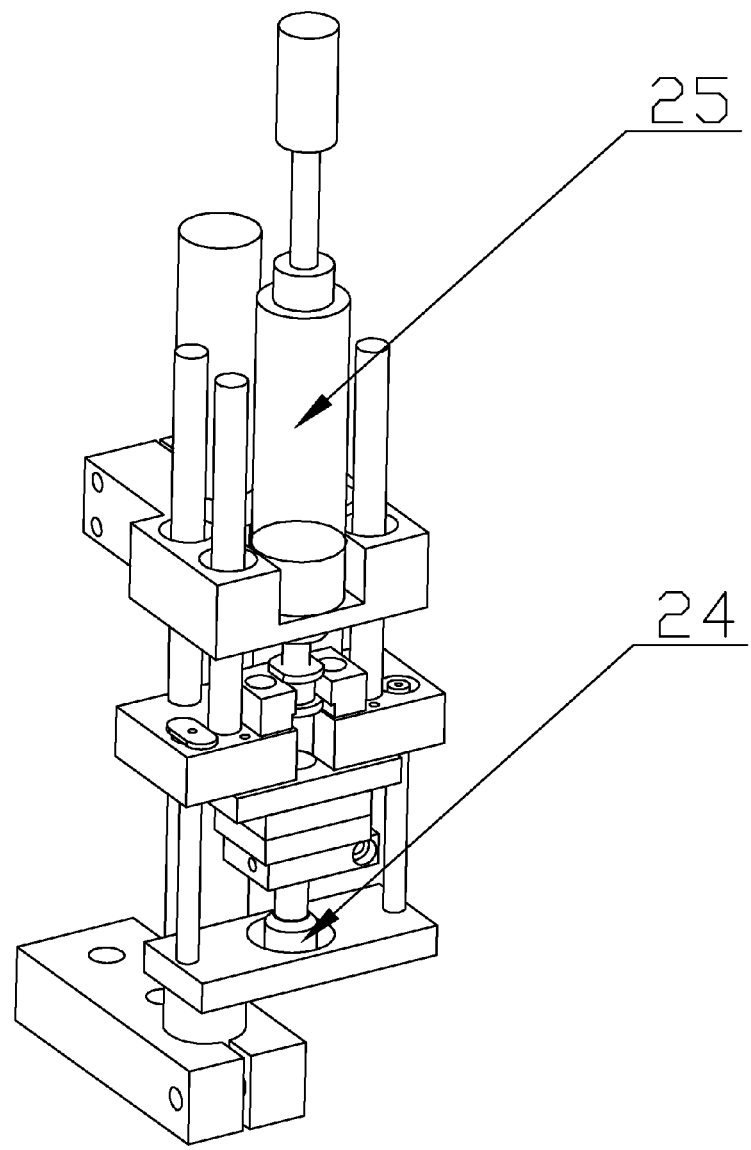
FIG. 7 is a structural schematic diagram of the automatic heat-sealing mechanism of the present invention.
Figure 8:
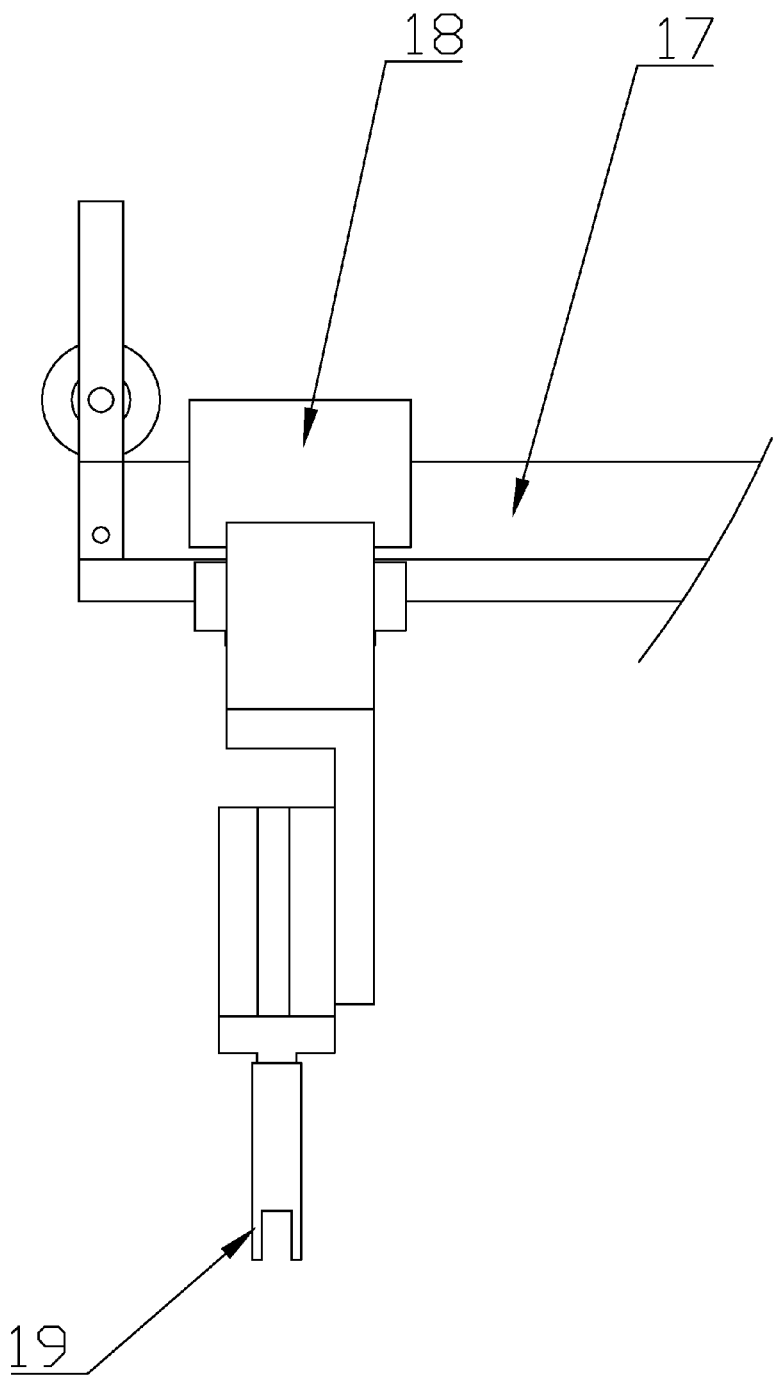
FIG. 8 is a structural schematic diagram of the automatic unloading mechanism of the present invention.

Referring to FIG. 1 to FIG. 8, an assembly machine for venting cap of disposable cell culture flask, comprising a rack 5, an automatic controller 7 and a rotating table 6 arranged on the rack 5, wherein an automatic loading mechanism 1, an automatic filter disc-sucking mechanism 2, an automatic heat-sealing mechanism 3, and an automatic unloading mechanism 4 are arranged above the rotating table 6; and the automatic controller 7 is electrically connected with the rotating table 6, the automatic loading mechanism 1, the automatic filter disc-sucking mechanism 2, the automatic heat-sealing mechanism 3, and the automatic unloading mechanism 4.

By means of the automatic loading mechanism 1, the automatic filter disc-sucking mechanism 2, the automatic heat-sealing mechanism 3 and the automatic unloading mechanism 4 as well as the automatic controller 7 and related control circuit adapted thereto, and with the control of automatic controller 7 to the automatic loading mechanism 1, the automatic filter disc-sucking mechanism 2, the automatic heat-sealing mechanism 3 and the automatic unloading mechanism 4, the present invention can realize the automatic loading of the venting cap of disposable cell culture flask, the automatic placing of the filter disc, and the automatic heat-sealing of the venting cap of disposable cell culture flask and the filter disc, so that the automatic production of the venting cap of disposable cell culture flask can be realized.

As a preferred embodiment of the present invention, the invention further comprises a lifting platform 10 arranged above the rotating table 6, wherein the automatic loading mechanism 1, the automatic filter disc-sucking mechanism 2 and the automatic unloading mechanism 4 are all arranged on the lifting platform 10 orderly, the lifting platform 10 can drive the automatic loading mechanism 1, the automatic filter disc-sucking mechanism 2, and the automatic unloading mechanism 4, so as to realize loading, mounting and unloading of the venting cap of disposable cell culture flask and the filter disc at the same time under the control of automatic controller 7.

As a preferred embodiment of the present invention, an loading guiding rail 11 is arranged within the automatic loading mechanism 1, one end of the loading guiding rail 11 is fixed on the lifting platform 10 and the other end is hanging; a loading sliding block 12 is arranged on the loading guiding rail 11; and a loading arm 13 is arranged below the loading sliding block 12. Under the control of the automatic controller 7, the lifting platform 10 lifts after the loading arm 13 has grasped the venting cap of disposable cell culture flask placed outside the rotating table 6. The loading sliding block 12 slides on the loading guiding rail 11 to move the loading arm 13 so as to convey the venting cap of disposable cell culture flask to a position above the rotating table 6. The lifting platform 10 descends, and the venting cap of disposable cell culture flask is released by the loading arm 13 which will put the venting cap of disposable cell culture flask on the rotating table 6. The lifting platform 10 lifts, and the loading arm 13 moves to the position above the venting cap of disposable cell culture flask. The lifting platform 10 descends, and the venting cap of disposable cell culture flask is grasped by the loading arm 13. With this cycle, the automatic loading of the venting cap of disposable cell culture flask can be realized. After the loading of the venting cap of disposable cell culture flask is completed, the venting cap of disposable cell culture flask is conveyed to loading position of filter disc under the action of the rotating table 6.

As a preferred embodiment of the present invention, a filter disc-sucking guiding rail 14 is arranged within the automatic filter disc-sucking mechanism 2, one end of the filter disc-sucking guiding rail 14 is fixed on the lifting platform 10 and the other end is hanging; a filter disc-sucking sliding block 15 is arranged on the filter disc-sucking guiding rail 14; and a filter disc-sucking end 16 is arranged below the filter disc-sucking sliding block 15. Under control of the automatic controller 7, the lifting platform 10 lifts after the filter disc-sucking end 16 has sucked the filter disc placed outside the rotating table 6. The filter disc-sucking sliding block 15 slides on the filter disc-sucking guiding rail 14, the lifting platform 10 descends after the filter disc is conveyed to a position above the venting cap of disposable cell culture flask. The filter disc can be placed within the venting cap of disposable cell culture flask after it is released by the filter disc-sucking end 16. The lifting platform 10 lifts, and the filter disc-sucking end 16 moves to a position above filter disc. The lifting platform 10 descends, and the filter disc is sucked by the filter disc-sucking end 16. With this cycle, the automatic loading of the filter disc can be realized. After the mounting of the filter disc is completed, the venting cap of disposable cell culture flask is conveyed to a heat-sealing position under the action of the rotating table 6.

As a preferred embodiment of the present invention, the automatic heat-sealing mechanism 3 is mounted on the rack 5, and a heat-sealing end 24 capable of moving vertically is arranged within the heat-sealing mechanism 3. The heat-sealing end 24 is connected to the output end of a cylinder 25. According to the control command of the automatic controller 7, the heat-sealing end 24 can be driven by the cylinder 25 and then move downward vertically, and the venting cap of disposable cell culture flask and the filter disc are bonded through heat-sealing by the heat-sealing end 24, so that the assemble of the venting cap of disposable cell culture flask and the filter disc is completed; and the heat-sealing end 24 can be driven by the cylinder 25 and then move upwards after the heat-sealing of the venting cap of disposable cell culture flask and the filter disc is completed, making the heat-sealing end 24 detach from the venting cap of disposable cell culture flask, and the venting cap of disposable cell culture flask is conveyed to a unloading position under the action of the rotating table 6.

As a preferred embodiment of the present invention, an unloading guiding rail 17 is arranged within the automatic unloading mechanism 4, one end of the unloading guiding rail 17 is fixed on the lifting platform 10 and the other end is hanging; and an unloading sliding block 18 is arranged on the unloading guiding rail 17 and an unloading arm 19 is arranged below the unloading sliding block 18. Under the control of the automatic controller 7, the lifting platform 10 lifts after the unloading arm 19 has grasped the finished venting cap of disposable cell culture flask placed within the rotating table 6. The unloading sliding block 18 slides on the unloading guiding rail 17 to move the unloading arm 19 so as to convey the finished venting cap of disposable cell culture flask to a position outside the rotating table 6. The finished venting cap of disposable cell culture flask is placed in a collection box after the lifting platform 10 descends. The lifting platform 10 lifts, and the unloading arm 19 moves to a position above the finished venting cap of disposable cell culture flask. The lifting platform 10 descends, and the venting cap of disposable cell culture flask is grasped by the unloading arm 19. With this cycle, the automatic unloading of the venting cap of disposable cell culture flask can be realized.

As a preferred embodiment of the present invention, a plurality of positioning fixtures 20 which are numbered orderly are arranged on the rotating table 6. The venting cap of disposable cell culture flask can be placed fixedly on the positioning fixture 20. The positioning fixture 20 can prevent the venting cap of disposable cell culture flask from displacing during the rotation of the rotating table 6. The automatic loading mechanism 1, the automatic filter disc-sucking mechanism 2, the automatic heat-sealing mechanism 3 and the automatic unloading mechanism 4 can be arranged orderly above the positioning fixtures 20 in different positions according to the actual requirement of production process.

In the present invention, a preferred embodiment is that eight positioning fixtures 20 are distributed uniformly on the rotating table 6, and the positions of the positioning fixtures 20 are numbered orderly in a clockwise direction. The automatic loading mechanism 1 is mounted above the positioning fixture in the first position, the automatic filter disc-sucking mechanism 2 is mounted above the positioning fixture in the third position, the automatic heat-sealing mechanism 3 is mounted above the positioning fixture in the sixth position, and the automatic unloading mechanism 4 is mounted above the positioning fixture in the seventh position. An induction controller 23 is arranged beside the positioning fixture between the automatic loading mechanism 1 and the automatic filter disc-sucking mechanism 2, the induction controller 23 can detect whether there is a venting cap of disposable cell culture flask on the positioning fixture in the position, and give feedback to the automatic controller 7 which makes a judgment and controls the action of the automatic filter disc-sucking mechanism 2.

As a preferred embodiment of the present invention, the invention further comprises a filter disc punching mould 8 which is arranged below the hanging end of the filter disc-sucking guiding rail 14. The filter sheet is punched by means of the filter disc punching mould 8 so as to form the filter disc of desired shape. The punched filter disc is conveyed to the venting cap of disposable cell culture flask by the filter disc-sucking end 16 under the action of the filter disc-sucking guiding rail 14, the filter disc-sucking sliding block 15 and the lifting platform 10.

Certainly, the present invention further comprises a filter sheet coiling-delivering mechanism and a filter sheet coiling-collecting mechanism, which can cooperate with the punching mould to accomplish the automatic production of the filter disc.

As a preferred embodiment of the present invention, the invention further comprises a feeding mechanism, wherein the feeding mechanism is provided with a vibration tray 21 and a feeding channel 22, and one end of the feeding channel 22 is connected with the vibration tray 21 and the other end is arranged below the hanging end of the loading guiding rail 11. While working, the venting cap of disposable cell culture flask can be placed within the vibration tray 21 and conveyed to tail end of the feeding channel 22 under the action of the vibration tray 21, and the venting cap of disposable cell culture flask at the tail end of the feeding channel 22 could be grasped by the loading arm 13 and conveyed to positioning fixture 20.

Certainly, the innovation of the present invention is not limited to the above-mentioned embodiments, those skilled in the art can also make equivalent modification or replacement without violating the spirit of present invention, and those equivalent modification or replacement are both included within the scope of the claim of the application.

What is claimed is:

1. An assembly machine for venting cap of disposable cell culture flask, the assembly machine comprising:
    a rack;
    an automatic controller and a rotating table arranged on the rack;
    an automatic loading mechanism, an automatic filter disc-sucking mechanism, an automatic heat-sealing mechanism and an automatic unloading mechanism are arranged above the rotating table; the automatic controller electrically connected with the rotating table, the automatic loading mechanism, the automatic filter disc-sucking mechanism, the automatic heat-sealing mechanism and the automatic unloading mechanism; and
    a lifting platform arranged above the rotating table, wherein the automatic loading mechanism, the automatic filter disc-sucking mechanism, and the automatic unloading mechanism are arranged on the lifting platform orderly, and wherein the automatic heat-sealing mechanism arranged between the automatic filter disc-sucking mechanism and the automatic unloading mechanism.

2. The assembly machine for venting cap of disposable cell culture flask according to claim 1, wherein the lifting platform is capable of driving the automatic loading mechanism, the automatic filter disc-sucking mechanism, and the automatic unloading mechanism to load, mount, and unload the venting cap.

3. The assembly machine for venting cap of disposable cell culture flask according to claim 1, further comprising:
    a loading guiding rail arranged within the automatic loading mechanism, one end of the loading guiding rail being fixed on the lifting platform and the other end hanging;
    a loading sliding block is arranged on the loading guiding rail; and
    a loading arm arranged below the loading sliding block.

4. The assembly machine for venting cap of disposable cell culture flask according to claim 3, further comprising a plurality of positioning fixtures arranged on the rotating table.

5. The assembly machine for venting cap of disposable cell culture flask according to claim 3, further comprising a feeding mechanism, the feeding mechanism including a vibration tray and a feeding channel, one end of the feeding channel being connected with the vibration tray and the other end being arranged below the hanging end of the loading guiding rail.

6. The assembly machine for venting cap of disposable cell culture flask according to claim 1, further comprising:
    a filter disc-sucking guiding rail arranged within the automatic filter disc-sucking mechanism, one end of the filter disc-sucking guiding rail fixed on the lifting platform and the other end is hanging;
    a filter disc-sucking sliding block arranged on the filter disc-sucking guiding rail; and
    a filter disc-sucking end arranged below the filter disc-sucking sliding block.

7. The assembly machine for venting cap of disposable cell culture flask according to claim 6, further comprising a filter disc punching mould, the filter disc punching mould being arranged below the hanging end of the filter disc-sucking guiding rail.

8. The assembly machine for venting cap of disposable cell culture flask according to claim 6, further comprising a plurality of positioning fixtures arranged on the rotating table.

9. The assembly machine for venting cap of disposable cell culture flask according to claim 6, further comprising a feeding mechanism, the feeding mechanism including a vibration tray and a feeding channel, one end of the feeding channel being connected with the vibration tray and the other end being arranged below the hanging end of the loading guiding rail.

10. The assembly machine for venting cap of disposable cell culture flask according to claim 1, wherein the automatic heat-sealing mechanism is mounted on the rack, and a heat-sealing end capable of moving vertically is arranged within the heat-sealing mechanism.

11. The assembly machine for venting cap of disposable cell culture flask according to claim 10, further comprising a plurality of positioning fixtures arranged on the rotating table.

12. The assembly machine for venting cap of disposable cell culture flask according to claim 10, further comprising a feeding mechanism, the feeding mechanism including a vibration tray and a feeding channel, one end of the feeding channel being connected with the vibration tray and the other end being arranged below the hanging end of the loading guiding rail.

13. The assembly machine for venting cap of disposable cell culture flask according to claim 1, further comprising:

an unloading guiding rail arranged within the automatic unloading mechanism, one end of the unloading guiding rail being fixed on the lifting platform and the other end is hanging;

an unloading sliding block arranged on the unloading guiding rail; and an unloading arm arranged below the unloading sliding block.

14. The assembly machine for venting cap of disposable cell culture flask according to claim 13, further comprising a plurality of positioning fixtures arranged on the rotating table.

15. The assembly machine for venting cap of disposable cell culture flask according to claim 13, further comprising a feeding mechanism, the feeding mechanism including a vibration tray and a feeding channel, one end of the feeding channel being connected with the vibration tray and the other end being arranged below the hanging end of the loading guiding rail.

16. The assembly machine for venting cap of disposable cell culture flask according to claim 1, further comprising a plurality of positioning fixtures arranged on the rotating table.

17. The assembly machine for venting cap of disposable cell culture flask according to claim 1, further comprising a feeding mechanism, the feeding mechanism including a vibration tray and a feeding channel, one end of the feeding channel being connected with the vibration tray and the other end being arranged below the hanging end of the loading guiding rail.

* * * * *

UNITED STATES PATENT AND TRADEMARK OFFICE
CERTIFICATE OF CORRECTION

| | |
|---|---|
| PATENT NO. | : 9,266,204 B2 |
| APPLICATION NO. | : 13/882164 |
| DATED | : February 23, 2016 |
| INVENTOR(S) | : Jianhua Yuan et al. |

It is certified that error appears in the above-identified patent and that said Letters Patent is hereby corrected as shown below:

Title Page, (75) Inventors: "Guangzhou, Japan" should be --Guangzhou City, CHINA--. (Both instances)

Signed and Sealed this
Seventeenth Day of May, 2016

Michelle K. Lee
*Director of the United States Patent and Trademark Office*